United States Patent
Chapuis

(10) Patent No.: US 10,472,591 B2
(45) Date of Patent: Nov. 12, 2019

(54) LILY OF THE VALLEY ODORANT

(71) Applicant: FIRMENICH SA, Geneva (CH)

(72) Inventor: Christian Chapuis, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 16/333,086

(22) PCT Filed: Dec. 18, 2017

(86) PCT No.: PCT/EP2017/083377
§ 371 (c)(1),
(2) Date: Mar. 13, 2019

(87) PCT Pub. No.: WO2018/114844
PCT Pub. Date: Jun. 28, 2018

(65) Prior Publication Data
US 2019/0225913 A1    Jul. 25, 2019

(30) Foreign Application Priority Data

Dec. 21, 2016    (EP) .................... 16205933

(51) Int. Cl.
| | | |
|---|---|---|
| *C11D 3/50* | (2006.01) | |
| *C11B 9/00* | (2006.01) | |
| *C07C 47/225* | (2006.01) | |
| *A61Q 19/10* | (2006.01) | |
| *A61K 8/33* | (2006.01) | |
| *A61Q 5/02* | (2006.01) | |
| *C11D 3/20* | (2006.01) | |

(52) U.S. Cl.
CPC .............. *C11B 9/0034* (2013.01); *A61K 8/33* (2013.01); *A61Q 5/02* (2013.01); *A61Q 19/10* (2013.01); *C07C 47/225* (2013.01); *C11D 3/2072* (2013.01); *C11D 3/50* (2013.01)

(58) Field of Classification Search
CPC ........... C11B 9/0034; A61K 8/33; A61Q 5/02; A61Q 19/10; C07C 47/225
See application file for complete search history.

(56) References Cited

U.S. PATENT DOCUMENTS

| 4,396,670 A | 8/1983 | Sinclair |
| 2013/0090390 A1 | 4/2013 | Singer et al. |

FOREIGN PATENT DOCUMENTS

WO    01/41915 A1    6/2001

OTHER PUBLICATIONS

M. Vinogradov et al., Zhurnal Organicheskoi Khimii 1974, vol. 10, pp. 1153-1157. No month available. (Year: 1974).*
International Search Report and Written Opinion, Appl. No. PCT/EP2017/083377, dated Mar. 8, 2018.
Bonatz et al., "Amino resin microcapsules. III. Release properties," Acta Polymerica, 40(11): 683-690, Nov. 1989.
Bône et al., "Microencapsulated Fragrances in Melamine Formaldehyde Resins," CHIMIA, 65(3): 177-181, Mar. 2011.
Dietrich et al., "Amino resin microcapsules. I. Literature and patent review," Acta Polymerica, 40(4): 243-251, Apr. 1989.
Dietrich et al., "Amino resins microcapsules. II. Preparation and morphology," Acta Polymerica, 40(5): 325-331, May 1989.
Dietrich et al., "Amino resin microcapsules. IV. Surface tension of the resins and mechanism of capsule formation," Acta Polymerica, 41(2): 91-95, Feb. 1990.
Lee et al., "Microencapsulation of fragrant oil via in situ polymerization: effects of pH and melamine-formaldehyde molar ratio," J. Microencapsulation, 2002, 19(5): 559-569.

* cited by examiner

*Primary Examiner* — John R Hardee
(74) *Attorney, Agent, or Firm* — Armstrong Teasdale LLP

(57) ABSTRACT

The present invention concerns a compound of formula (I) in the form of any one of its stereoisomers or as a mixture thereof, and wherein carbon 4 of the cyclohexenyl group has an absolute S configuration and R represents a hydrogen atom or a methyl group and their use in perfumery to impart odor notes of white peach and floral type.

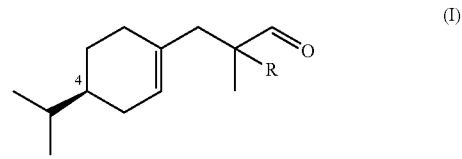

(I)

11 Claims, No Drawings

LILY OF THE VALLEY ODORANT

This application is a 371 filing of International Patent Application PCT/EP2017/083377 filed Dec. 18, 2017, which claims the benefit of European application no. EP 16205933.1 filed Dec. 21, 2016.

TECHNICAL FIELD

The present invention relates to the field of perfumery. More particularly, it concerns the use as perfuming ingredient of compound of formula (I) as defined below, which is useful perfuming ingredient of white peach, floral type. Therefore, following what is mentioned herein, the present invention comprises the invention's compound as part of a perfuming composition or of a perfuming consumer product.

PRIOR ART

One of the most sought ingredients in the perfumery field are the ones imparting a floral impression and in particular a lily of the valley odor. Said note is very appreciated and used in a multitude of perfumed consumer products. Since decades, a lot of efforts have been put in order to obtain compounds possessing this very complex white floral odor, especially since the use of Lilial® (2-methyl-3-[4-(2-methyl-2-propanyl)phenyl]propanal, trademark from Givaudan-Roure SA, Vernier, Suisse) representing one of the most valuable perfuming ingredients with a lily of the valley and watery connotation, has been limited due to various reasons.

So, there is a need to develop novel perfuming ingredients conferring a floral odor note being as close as possible to the natural odor of the lily of the valley blossom.

US 2013/0090390 reports as a compound imparting said olfactive properties 3-(4-isopropylcyclohex-1-en-1-yl)propanal. In particular, (R)-3-(4-isopropylcyclohex-1-en-1-yl)propanal imparts a lily of the valley, floral, sweet, watery, powdery and ozone-like note, whereas (S)-3-(4-isopropylcyclohex-1-en-1-yl)propanal is less preferred and confers a lily of the valley, fruity, green, watery and aldehydic-like note. Said document also mentions 3-(4-isopropylcyclohex-1-en-1-yl)-2-methylpropanal without making any distinction between the odors of each diastereoisomer. However, this compound despite its structural similarity with 3-(4-isopropylcyclohex-1-en-1-yl)propanal confers aldehyde-like, sweet, watery and floral of type cyclamen odor devoid of lily of valley notes. This document is silent toward the stereochemistry of this molecule letting assume that the odor corresponds to the odor of a mixture comprising the four diastereoisomers.

The present invention provides a novel perfumery ingredient imparting lily of the valley note, by using compound of formula (I) which also possesses white peach connotation. The organoleptic properties of compound of formula (I) have never been mentioned.

The prior art document mentioned above does not report or suggest any organoleptic properties of the compound of formula (I), or any use of said compound in the field of perfumery.

SUMMARY OF THE INVENTION

The invention relates to compound of formula (I) which imparts in addition to lily of valley odor note, a white peach odor note and its use as a perfuming ingredient. The combination of both odors is very rare.

So, a first embodiment of the present invention is a compound of formula

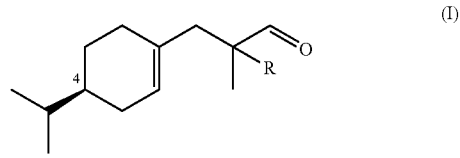

in the form of any one of its stereoisomers or as a mixture thereof, wherein carbon 4 of the cyclohexenyl group has an absolute S configuration and R represents a hydrogen atom or a methyl group.

An embodiment object of the present invention is a method to confer, enhance, improve or modify the odor properties of a perfuming composition or of a perfumed article, which method comprises adding to said composition or article an effective amount of at least one compound of formula (I) as defined above.

Another embodiment of the present invention is a perfuming composition comprising
i) at least one compound of formula (I), as defined above;
ii) at least one ingredient selected from the group consisting of a perfumery carrier and a perfumery base; and
iii) optionally at least one perfumery adjuvant.

A last embodiment of the present invention is a perfumed consumer product comprising at least one compound of formula (I) or a composition as defined above.

DESCRIPTION OF THE INVENTION

Surprisingly, it has now been discovered that compound of formula (I), having an absolute S configuration on the carbon bearing the isopropyl group, possess an odor note very interesting with lily of the valley connotation which is particularly appreciated. Those compounds have also never been disclosed.

A first object of the present invention is a compound of formula

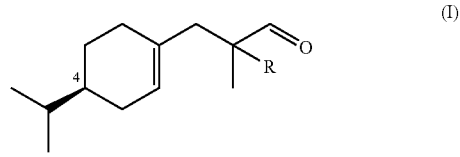

in the form of any one of its stereoisomers or as a mixture thereof, wherein carbon 4 of the cyclohexenyl group has an absolute S configuration and R represents a hydrogen atom or a methyl group. Said compound can be used as perfuming ingredient, for instance to impart odor notes of the lily of the valley type with a white peach connotation.

For the sake of clarity, by the expression "any one of its stereoisomers", or the similar, it is meant the normal meaning understood by a person skilled in the art, i.e. that the invention compounds can be a pure or be in the form of a mixture of diastereoisomers, provided of course that the carbon 4 of the cyclohexenyl group has an absolute S configuration. The invention's compound may be (R)-3-((S)-4-isopropylcyclohex-1-en-1-yl)-2-methylpropanal, (S)-3-((S)-4-isopropylcyclohex-1-en-1-yl)-2-methylpropanal or a mixture thereof. Preferably, the invention's compound may be in a form of a mixture comprising (R)-3-((S)-4-isopropylcyclohex-1-en-1-yl)-2-methylpropanal in an amount comprised between 35 wt % and 65 wt % and (S)-3-((S)-4-isopropylcyclohex-1-en-1-yl)-2-methylpropanal in an amount comprised between 35 wt % and 65 wt %.

According to any one of the above embodiment, the invention's compound is of formula

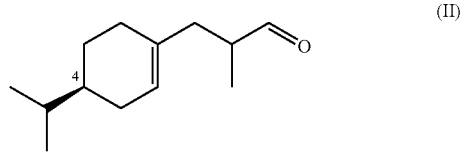

(II)

in the form of any one of its stereoisomers or as a mixture thereof, wherein carbon 4 of the cyclohexenyl group has an absolute S configuration.

As a specific example of the invention's compounds, one may cite, 3-((S)-4-isopropylcyclohex-1-en-1-yl)-2-methylpropanal which has a powerful lily of the valley and watery odor typical of the Lilial® comprising some hesperidia and lactonic white peach twist which is a rare combination for perfumery ingredients. Said compound is characterized by an odor having lily of the valley and watery notes duality as Lilial®, comprising also petaly and velvety connotations. The isomer 3-((R)-4-isopropylcyclohex-1-en-1-yl)-2-methylpropanal is less powerful and possesses an aldehydic-metallic top note whereas the floral aspect with the watery and lily of the valley duality is less present which make it less interesting in an organoleptic point of view. Moreover, a mixture comprising 3-((S)-4-isopropylcyclohex-1-en-1-yl)-2-methylpropanal and 3-((R)-4-isopropylcyclohex-1-en-1-yl)-2-methylpropanal in a 1 to 1 ratio, which should correspond to 3-(4-isopropylcyclohex-1-en-1-yl)-2-methylpropanal disclosed US 2013/0090390, is less strong and diffusive that the invention's compound and loses its freshness and its cyclamen florally becoming more fatty-aldehydic and metallic.

As another specific example of the invention's compounds, one may cite, (S)-3-(4-isopropyl-1-cyclohexen-1-yl)-2,2-dimethylpropanal which possesses an odor similar to the 3-((S)-4-isopropylcyclohex-1-en-1-yl)-2-methylpropanal being a slightly less powerful.

The organoleptic properties of the invention's compounds and of the prior art compound are summed up in Table 1.

TABLE 1

| Compounds and their odor properties | |
|---|---|
| Compound structure and name | Odor notes |
| 3-((S)-4-isopropylcyclohex-1-en-1-yl)-2-methylpropanal | lily of the valley, watery, hesperidia and lactonic white peach |
| 3-((S)-4-isopropylcyclohex-1-en-1-yl)-2,2-dimethylpropanal | lily of the valley, watery and lactonic white peach |
| 3-((R)-4-isopropylcyclohex-1-en-1-yl)-2-methylpropanal | aldehydic-metallic, less floral-muguet, less powerful |
| Prior art compound | |
| 3-(4-isopropylcyclohex-1-en-1-yl)-2-methylpropanal | fatty-aldehydic and metallic less strong and diffusive |

When the odor of the invention's compounds is compared with that of the prior art compound, i.e. 3-(4-isopropylcyclohex-1-en-1-yl)-2-methylpropanal as reported in US 2013/0090390, the invention's compound distinguishes themselves by a clearly more powerful and diffusive note having a water melon odor and a characteristic lactonic aspect reminiscent of the white peach and by lacking the aldehydic note characteristic of the prior art compound(s). Moreover the invention's compound, contrary to the prior art, besides a lily of the valley—watery note, shows an odor that is allied with a texture of peach skin such as velvety and petali. The odors of the invention's compound are also lacking, or not possessing significant sweet notes which are characteristic of the prior art compounds. Said differences lend the invention's compounds and the prior art compounds to be each suitable for different uses, i.e. to impart different organoleptic impressions.

As mentioned above, the invention concerns the use of a compound of formula (I) as a perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note.

By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:

i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic materials, such as porous polymers, cyclodextrines, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As other non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine, such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. in Journal of Microencapsulation, 2002, vol. 19, pages 559-569, international patent publication WO 01/41915 or yet the article of S. Bône et al. in Chimia, 2011, vol. 65, pages 177-181.

By "perfumery base", what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:

Aldehydic ingredients: decanal, dodecanal, 2-methyl-undecanal, 10-undecenal, octanal and/or nonenal;

Aromatic-herbal ingredients: eucalyptus oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients: Methyl dihydrojasmonate, linalool, Citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-diméthyléthyl)-1-cyclohexyl acetate, verdyl isobutyrate and/or mixture of methylionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-Dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, pentadecenolide, 3-Methyl-5-cyclopentadecen-1-one, 1,3,4,6,7,8-hexahydro-4,6,6,7,8,8-hexamethylcyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" it is meant here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungi or anti irritant agents), abrasives, skin cooling agents, fixatives, insect repellents, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compounds can also be advantageously used in all the fields of modern perfumery, i.e. fine or functional perfumery, to positively impart or modify the odor of a consumer product into which said compound (I) is added. Consequently, another object of the present invention consists of a perfumed consumer product comprising, as a perfuming ingredient, at least one compound of formula (I), as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care, a wipe, a dish detergent or a hard-surface (e.g. a floor, bath, sanitary or a windows) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. In the case of perfumed consumer product, typical concentrations are in the order of 0.0001% to 1% by weight, or even more, of the compounds of the invention based on the weight of the consumer product into which they are incorporated.

The invention's compounds can be prepared according to a method as described herein-below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

a) Preparation of Ethyl 3-((S)-4-isopropylcyclohex-1-en-1-yl)-2-methylpropanoate (Compound A)

Alcohol (5S)-5-isopropyl-2-methylenecyclohexan-1-ol obtained from (−)-(S)-limonene according to US 2013/0090390 (18.2 g, 0.118 mol), ethyl orthopropionate (71.2 ml, 0.355 mmol) and pivalic acid (1.18 g, 0.011 mol) was heated at 120° C. for 1 h, then 150° for 2 h. After distillation of EtOH and the excess of ethyl orthopropionate, the cold mixture was extracted with $Et_2O$, washed with 15% aq. NaOH, then $H_2O$ to neutrality, dried, concentrated and bulb-to-bulb distilled to afford Compound A in 79.3% yield as a 2:3 mixture of stereoisomer (Bp. 118° C./2.4 mbar, $α_D^{20}$=−55.4 neat).

IR: 2958, 1736, 1458, 1374, 1176.

$^1$H-NMR: major 5.41 (brs, 1H); 4.11 (q, J=7.2, 2H); 2.64-2.53 (m, 1H); 2.35-2.28 (m, 1H); 2.04-1.89 (m, 4H); 1.79-1.68 (m, 2H); 1.51-1.39 (m, 1H); 1.24 (t, J=7.2, 3H); 1.21-1.14 (m, 2H); 1.09 (d, J=7.2, 3H); 0.88 (d, J=6.7, 3H); 0.87 (d, J=6.7, 3H); minor 5.41 (brs, 1H); 4.10 (q, J=7.2, 2H); 2.64-2.53 (m, 1H); 2.35-2.28 (m, 1H); 2.04-1.89 (m, 4H); 1.79-1.68 (m, 2H); 1.51-1.39 (m, 1H); 1.24 (t, J=7.2, 3H); 1.21-1.14 (m, 2H); 1.10 (d, J=7.2, 3H); 0.88 (d, J=6.7, 3H); 0.87 (d, J=6.7, 3H).

$^{13}$C-NMR: major 176.8 (s); 134.8 (s); 123.3 (d); 60.1 (t); 42.0 (t); 40.1 (d); 37.9 (d); 32.2 (d); 29.0 (t); 28.7 (t); 26.4 (t); 20.0 (q); 19.7 (q); 16.6 (q); 14.3 (q); minor 176.8 (s); 134.8 (s); 123.3 (d); 60.1 (t); 42.0 (t); 40.1 (d); 38.1 (d); 32.2 (d); 29.0 (t); 28.7 (t); 26.5 (t); 20.0 (q); 19.7 (q); 16.9 (q); 14.3 (q). MS: major 238 (11, M$^{+•}$), 192 (33), 164 (10), 149 (12), 137 (62), 121 (46), 109 (21), 107 (20), 102 (100), 95 (46), 93 (47), 81 (79), 79 (52), 74 (41), 67 (29), 55 (30), 41 (52), 29 (27); minor 238 (10, M$^{+•}$), 192 (31), 164 (10), 149 (13), 137 (62), 121 (46), 109 (20), 107 (18), 102 (100), 95 (46), 93 (45), 81 (80), 79 (48), 74 (43), 67 (28), 55 (29), 41 (47), 29 (33).

b) Preparation of 3-((S)-4-Isopropylcyclohex-1-en-1-yl)-2-methylpropan-1-ol (Compound B)

A solution of Compound A (21.06 g, 88.5 mmol) in $Et_2O$ (17.7 ml) was added dropwise to a suspension of $LiAlH_4$ (2.52 g, 66.36 mmol) in $Et_2O$ (26.3 ml). After 1 h, $H_2O$ (2.5 ml), 15% aq. NaOH (2.5 ml), then $H_2O$ (7.5 ml) were successively added and the resulting mixture was filtered over Celite, then concentrated. Bulb-to-bulb distillation afforded Compound B in 66-88% yield as a 56:44 mixture of stereoisomer (Bp 91° C./1 mbars, $α_D^{20}$=−72.2, neat).

IR: 3333, 2956, 1464, 1435, 1380, 1360, 1036.

$^1$H-NMR: 5.43 (brs, 1H); 3.53-3.39 (m, 2H); 2.07-1.94 (m, 5H); 1.88-1.72 (m, 5H); 1.51-1.42 (m, 1H); 1.47 (brs, 1 OH); 1.30-1.13 (m, 3H); 0.89 (d, J=6.7, 3H); 0.87 (d, J=6.7, 3H).

$^{13}$C-NMR: major 136.3 (s); 122.8 (d); 68.6 (t); 42.3 (t); 40.2 (d); 33.6 (d); 32.3 (d); 29.0 (2t); 26.5 (t); 20.0 (q); 19.7 (q); 16.6 (q); minor 136.3 (s); 122.8 (d); 68.4 (t); 42.4 (t); 40.2 (d); 33.6 (d); 32.3 (d); 29.0 (2t); 26.5 (t); 20.0 (q); 19.7 (q); 17.1 (q).

MS: 196 (11, M$^{+\cdot}$), 165 (11), 138 (50), 135 (38), 123 (17), 121 (13), 109 (32), 107 (29), 95 (65), 93 (88), 91 (34), 83 (52), 81 (64), 79 (89), 77 (39), 69 (51), 67 (59), 65 (13), 58 (45), 55 (49), 53 (23), 43 (46), 41 (100), 39 (35), 31 (58), 27 (35).

c) Preparation of 3-((S)-4-Isopropylcyclohex-1-en-1-yl)-2-methylpropanal (Compound C)

A suspension of Compound B (9.95 g, 50.8 mmol), PCC (16.4 g, 76.15 mmol), and Celite (24.6 g) in CH$_2$Cl$_2$ (112 ml) was stirred for 2 h. The mixture was filtered over SiO$_2$ (10 g), concentrated, diluted with Et$_2$O, then washed with 15% aq. HCl, then NaHCO$_3$, and H$_2$O, dried, concentrated, and bulb-to-bulb distilled to afford Compound C in 90% yield as a 56:44 mixture of stereoisomer (Bp. 75° C./0.22 mbars, $\alpha_D^{20}$=−68.1, neat).

IR: 2958, 1728, 1457, 1440, 1386.

$^1$H-NMR: major 9.62 (d, J=3.3, 1H); 5.44 (brs, 1H); 2.55-2.45 (m, 1H); 2.41-2.33 (m, 1H); 2.06-1.90 (m, 4H); 1.80-1.69 (m, 2H); 1.51-1.41 (m, 1H); 1.27-1.16 (m, 2H); 1.04 (d, J=6.8, 3H); 0.89 (d, J=6.8, 3H); 0.87 (d, J=6.8, 3H); minor 9.61 (d, J=2.3, 1H); 5.44 (brs, 1H); 2.55-2.45 (m, 1H); 2.41-2.33 (m, 1H); 2.06-1.90 (m, 4H); 1.80-1.69 (m, 2H); 1.51-1.41 (m, 1H); 1.27-1.16 (m, 2H); 1.045 (d, J=6.8, 3H); 0.89 (d, J=6.8, 3H); 0.87 (d, J=6.8, 3H).

$^{13}$C-NMR: major 205.4 (d); 134.0 (s); 123.9 (d); 44.5 (d); 40.1 (d); 38.9 (t); 32.2 (d); 29.0 (2t); 26.3 (t); 20.0 (q); 19.7 (q); 13.2 (q); minor 205.4 (d); 134.1 (s); 123.9 (d); 44.4 (d); 40.1 (d); 38.9 (t); 32.2 (d); 29.0 (2t); 26.4 (t); 20.0 (q); 19.7 (q); 13.5 (q)

MS: 194 (14, M$^{+\cdot}$), 152 (30), 136 (23), 133 (18), 123 (23), 121 (18), 109 (35), 95 (40), 93 (100), 91 (44), 81 (84), 79 (52), 77 (40), 69 (22), 67 (50), 65 (13), 55 (35), 53 (21), 43 (38), 41 (82), 39 (33), 29 (33), 27 (34).

d) Preparation of 3-((S)-4-Isopropylcyclohex-1-en-1-yl)-2,2-dimethylpropanal (Compound D)

Compound C (7.3 g, 37.6 mmol.) was added dropwise to a solution of tBuOK (5.05 g, 45.1 mmol.) in tBuOH (37.6 ml) below 35° C. Then MeI (2.81 ml, 45.1 mmol.) was added and after 2 h, the mixture was diluted with Et$_2$O, extracted with H$_2$O to neutrality, dried (Na$_2$SO$_4$), concentrated and bulb-to-bulb distilled to afford Compound D in 69% yield.

Bp: 80° C./0.38 mbar. $\alpha_D^{20}$=−63.3; $[\alpha]_D^{20}$=−78.3, c=2.52, CHCl$_3$.

IR: 2958, 2917, 2872, 2839, 2694, 1727, 1466, 1436, 1385, 1366, 908, 875, 819, 776, 752.

$^1$H-NMR: 9.53 (s, 1H); 5.40 (brs, 1H); 2.17 (qAB, J=14.3, 2H); 2.05-1.99 (m, 1H); 1.93-1.69 (m, 4H); 1.44 (oct, J=6.6, 1H); 1.23-1.11 (m, 2H); 1.03 (s, 6H); 0.87 (d, J=6.6, 3H); 0.86 (d, J=6.6, 3H).

$^{13}$C-NMR: 206.6 (d); 133.7 (s); 125.8 (d); 46.4 (s); 46.0 (t); 39.8 (d); 32.2 (d); 31.0 (t); 29.1 (t); 26.5 (t); 22.2 (q); 21.5 (q); 19.9 (q); 19.6 (q).

MS: 208 (9, M$^{+\cdot}$), 193 (11), 152 (50), 137 (18), 124 (19), 121 (15), 109 (25), 95 (58), 93 (60), 91 (25), 81 (100), 79 (35), 77 (23), 72 (18), 70 (54), 67 (32), 55 (22), 43 (31), 41 (40).

Example 2

Synthesis of 3-((R)-4-isopropylcyclohex-1-en-1-yl)-2-methylpropanal (Outside the Scope of the Invention)

3-((R)-4-isopropylcyclohex-1-en-1-yl)-2-methylpropanal was prepared following the method described in example 1 starting from (5R)-5-isopropyl-2-methylenecyclohexan-1-ol obtained from (+)-(R)-limonene according to US 2013/0090390. 3-((R)-4-isopropylcyclohex-1-en-1-yl)-2-methylpropanal was obtained with the similar yield than 3-((S)-4-isopropylcyclohex-1-en-1-yl)-2-methylpropanal ($\alpha_D^{20}$=+78.6, neat).

Example 3

Preparation of a Perfuming Composition

A perfuming composition for fabric softener, was prepared by admixing the following ingredients:

| Parts by weight | Ingredient |
|---|---|
| Benzyl acetate | 600 |
| Carbinol acetate | 100 |
| (Z)-3-hexen-1-ol acetate | 20 |
| Cinnamic alcohol | 100 |
| Anisic aldehyde | 40 |
| C 12 Aldehyde | 10 |
| Hexylcinnamic aldehyde | 1400 |
| Allyl amyl glycolate | 40 |
| Methyl anthranilate | 20 |
| Gamma undecalactone | 100 |
| Nitrile citronellyl | 20 |
| Verdyle acetate | 200 |
| Verdyle propionate | 100 |
| Damascone alpha | 10 |
| Dartanol ® [1] | 140 |
| Dihydromyrcenol | 400 |
| Diphenyl oxyde | 100 |
| Eugenol | 100 |
| Habanolide ® [2] | 1000 |
| Hedione ® [3] | 1000 |
| Phenethylol | 1000 |
| Rosinol[4] | 40 |
| Amyle salicylate | 1200 |
| Terpineol | 1000 |
| Verdox ™ [5] | 200 |
| Ylang essential oil | 60 |
| | 9000 |

[1] (1'R,E)-2-ethyl-4-(2',2',3'-trimethyl-3'-cyclopenten-1'-yl)-2-buten-1-ol; origin: Firmenich SA, Geneva, Switzerland
[2] Pentadecenolide; origin: Firmenich SA, Geneva, Switzerland
[3] Methyl dihydrojasmonate; origin: Firmenich SA, Geneva, Switzerland
[4] 2,2,2-trichloro-1-phenylethyl acetate; origin: Firmenich SA, Geneva, Switzerland
[5] 2-tert-butyl-1-cyclohexyl acetate; origin: International Flavors & Fragrances, USA The addition of 1000 parts by weight of 3-((S)-4-isopropylcyclohex-1-en-1-yl)-2-methylpropanal to the above-described composition imparted to the latter distinctly fresh cyclamen and lily of the valley connotation and conferred more watery freshness to its top and bottom note.

When, instead of the invention's compound, the same amount of 3-((R)-4-isopropylcyclohex-1-en-1-yl)-2-methylpropanal was used, the composition acquired a slightly more fatty-aldehydic but also a more metallic connotation. The effect observed is rather weak and not positive.

When instead of the invention's compound, the same amount of Mugoxal® (3-(4-tert-butyl-1-cyclohexen-1-yl) propanal; origin: Firmenich SA, Geneva, Switzerland) was used, the composition acquired a distinctly elegant and sparkling lily of the valley white flower connotation but devoid of the lactonic white peach note.

When instead of the invention's compound, the same amount of (−)-(S)-3-(4-isopropylcyclohex-1-en-1-yl)propanal reported in US 2013/0090390, was used, the results was totally different as the composition acquired a distinctly clean aldehydic, citrus-lime and mandarine connotation which is classical in this kind of notes. Said compound imparted an aldehydic-citrus note instead of a floral note.

When instead of the invention's compound were used the same amount of (+−)-2-methyl-3-[4-(2-methyl-2-propanyl)-1-cyclohexen-1-yl]propanal, the composition acquired a lily of the valley connotation reminiscent of Lilial® but devoid of the lactonic white peach note.

Example 4

Preparation of a Fabric Softener Comprising the Invention's Compound

TABLE 1

Composition of the softener formulation

| Ingredient | Concentration [wt %] |
|---|---|
| Methyl bis[ethyl (tallowate)]-2-hydroxyethyl ammonium methyl sulfate[1] | 12.20 |
| 1,2-benzisothiazolin-3-one[2] | 0.04 |
| CaCl$_2$ (10% aqueous solution) | 0.40 |
| Water | 87.36 |

[1] Stepantex VL90 A Diester Quat; Origin: Stepan
[2] Proxel GXL; Origin: Arch

The softener was prepared by weighting Methyl bis[ethyl (tallowate)]-2-hydroxyethyl ammonium methyl sulfate which was heated at 65° C. Then Water and 1,2-benzisothiazolin-3-one were placed in the reactor and were heated at 65° C. under stirring.

To the above mixture was added Methyl bis[ethyl (tallowate)]-2-hydroxyethyl ammonium methyl sulfate. The mixture was stirred 15 minuted and CaCl$_2$ was added.

Then 0.5 to 2% by weight, relative to the total weight of the softener, of the invention's composition of example 3 was added. The mixture was stirred 15 minutes and was cooled down to room temperature under stirring (viscosity measure: result 35+/−5 mPas. (shear rate 106 sec-1)).

Example 5

Preparation of a Liquid Detergent Comprising the Invention's Compound

TABLE 2

Composition of the liquid detergent formulation

| Ingredients | Concentration [wt %] |
|---|---|
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene Glycol | 11 |
| Citric acid | 6.5 |
| Potassium Hydroxyde | 9.5 |
| Properase L[4] | 0.2 |
| Puradax EG L[4] | 0.2 |
| Purastar ST L[4] | 0.2 |
| Acrylates/Steareth-20 Methacrylate structuring Crosspolymer[5] | 6 |
| Deionized Water | 27.4 |

[1] Hostapur SAS 60; Origin: Clariant
[2] Edenor K 12-18; Origin: Cognis
[3] Genapol LA 070; Origin: Clariant
[4] Origin: Genencor International
[5] Aculyn 88; Origin: Dow Chemical The liquid detergent was prepared by adding 0.5 to 1.5% by weight, relative to the total weight of the liquid detergent, of the invention's composition of example 3 into the unperfumed liquid detergent formulation of Table 2 under gentle shaking.

Example 6

Preparation of a Transparent Isotropic Shampoo Comprising the Invention's Composition

TABLE 3

Composition of the transparent isotropic shampoo formulation

| Phases | Ingredients | Concentration [wt %] |
|---|---|---|
| A | Water deionized | 44.4 |
|  | Polyquaternium-10 [1] | 0.3 |
|  | Glycerin 85% [2] | 1 |
|  | DMDM Hydantoin [3] | 0.2 |
| B | Sodium Laureth Sulfate [4] | 28 |
|  | Cocamidopropyl Betaine [5] | 3.2 |
|  | Disodium Cocoamphodiacetate [6] | 4 |
|  | Ethoxy (20) Stearyl Alcohol [6] | 1 |
| C | Sodium Laureth Sulfate [4] | 3 |
|  | Glyceryl Laureate [7] | 0.2 |
| D | Water deionized | 1 |
|  | Sodium Methylparaben [8] | 0.1 |
| E | Sodium Chloride 10% aqueous sol. | 15 |
|  | Citric acid 10% aqueous sol. till pH 5.5-6 | q.s. |

[1] Ucare Polymer JR-400, Origin: Noveon
[2] Origin: Schweizerhall
[3] Glydant, Origin: Lonza
[4] Texapon NSO IS, Origin: Cognis
[5] Tego Betain F 50, Origin: Evonik
[6] Amphotensid GB 2009, Origin: Zschimmer & Schwarz
[7] Monomuls 90 L-12, Origin: Gruenau
[8] Nipagin Monosodium, Origin: NIPA The shampoo was prepared by dispersed in water Polyquatemium-10. The remaining ingredients of phase A were mixed separately by addition of one after the other while mixing well after each adjunction. This pre-mix was added to the Polyquaternium-10 dispersion and mixed for another 5 min. Then, the premixed phase B and the premixed Phase C were added (Monomuls 90L-12 was heated to melt in Texapon NSO IS) while agitating. Phase D and Phase E were added while agitating. PH was adjusted with citric acid solution till pH: 5.5-6.0 leading to an unperfumed shampoo formulae.

The perfumed shampoo was prepared by adding 0.4 to 0.8% by weight, relative to the total weight of the shampoo, of the invention's composition of example 3 into the unperfumed shampoo formulation of Table 3 under gentle shaking.

Example 7

Preparation of a Structured Shower Gel Comprising the Invention's Composition

TABLE 4

Composition of the shower gel formulation

| Ingredients | Amount (% wt) |
| --- | --- |
| WATER deionised | 49.350 |
| Tetrasodium EDTA [1] | 0.050 |
| Acrylates Copolymer [2] | 6.000 |
| Sodium C12-C15 Pareth Sulfate [3] | 35.000 |
| Sodium Hydroxide 20% aqueous solution | 1.000 |
| Cocamidopropyl Betaine [4] | 8.000 |
| Methylchloroisothiazolinone and Methylisothiazolinone [5] | 0.100 |
| Citric Acid (40%) | 0.500 |

[1] EDETA B POWDER; trademark and origin: BASF
[2] CARBOPOE AQUA SF-1 POLYMER; trademark and origin: NOVEON
[3] ZETESOL AO 328 U; trademark and origin: ZSCHIMMER & SCHWARZ
[4] TEGO-BETAIN F 50; trademark and origin: GOLDSCHMIDT
[5] KATHON CG; trademark and origin: ROHM & HASS The shower gel was prepared by adding 0.5 to 1.5% by weight, relative to the total weight of the shower gel, of the invention's composition of example 3 into the unperfumed shower gel formulation of Table 4 under gentle shaking.

Example 8

Preparation of a Transparent Shower Gel Comprising the Invention's Composition

TABLE 5

Composition of the transparent shower gel formulation

| Ingredients | Concentration (% wt) |
| --- | --- |
| WATER deionized | 52.40 |
| Tetrasodium EDTA [1] | 0.10 |
| Sodium Benzoate | 0.50 |
| Propylene Glycol | 2.00 |
| Sodium C12-C15 Pareth Sulfate [2] | 35.00 |
| Cocamidopropyl Betaine [3] | 8.00 |
| Polyquaternium-7 [4] | 0.20 |
| Citric Acid (40%) | 1.00 |
| Sodium Chloride | 0.80 |

[1] EDETA B POWDER; trademark and origin: BASF
[2] ZETESOL AO 328 U; trademark and origin: ZSCHIMMER & SCHWARZ
[3] TEGO-BETAIN F 50; trademark and origin: GOLDSCHMIDT
[4] MERQUAT 550; trademark and origin: LUBRIZOL The transparent shower gel was prepared by adding 0.5 to 1.5% by weight, relative to the total weight of the shower gel, of the invention's composition of example 3 into the unperfumed shower gel formulation of Table 5 under gentle shaking.

Example 9

Preparation of a Milky Shower Gel Comprising the Invention's Composition

TABLE 6

Composition of the milky shower gel formulation

| Ingredients | Concentration (% wt) |
| --- | --- |
| WATER deionized | 50.950 |
| Tetrasodium EDTA [1] | 0.050 |
| Sodium Benzoate | 0.500 |
| Glycerin 86% | 3.500 |
| Sodium Laureth Sulfate [2] | 27.000 |
| Polyquaternium-7 [3] | 1.000 |
| Coco-Betaine [4] | 6.000 |
| PEG-120 Methyl Glucose trioleate [5] | 1.000 |
| Citric Acid (40%) | 1.000 |
| Glycol Distearate & Laureth-4 & Cocamidopropyl Betaine [6] | 3.000 |
| Sodium Chloride 20% | 5.000 |
| PEG-40 Hydrogenated Castor Oil [7] | 1.000 |

[1] EDETA B POWDER; trademark and origin: BASF
[2] Texapon NSO IS; trademark and origin: COGNIS
[3] MERQUAT 550; trademark and origin: LUBRIZOL
[4] DEHYTON AB-30; trademark and origin: COGNIS
[5] GLUCAMATE LT; trademark and origin: LUBRIZOL
[6] EUPERLAN PK 3000 AM; trademark and origin: COGNIS
[7] CREMOPHOR RH 40; trademark and origin: BASF The transparent shower gel was prepared by adding 0.5 to 1.5% by weight, relative to the total weight of the shower gel, of the invention's composition of example 3 into the unperfumed shower gel formulation of Table 6 under gentle shaking.

Example 10

Preparation of a Pearly Shampoo Comprising the Invention's Composition

TABLE 7

Composition of the pearly isotropic shampoo formulation

| Phases | Ingredients | Concentration (% wt) |
| --- | --- | --- |
| A | Water deionized | 45.97 |
|   | Tetrasodium EDTA [1] | 0.05 |
|   | Guar Hydroxypropyltrimonium Chloride [2] | 0.05 |
|   | Polyquaternium-10 [3] | 0.075 |
| B | NaOH 10% aqueous sol. | 0.3 |
| C | Ammonium Lauryl Sulfate [4] | 34 |
|   | Ammonium Laureth Sulfate [5] | 9.25 |
|   | Cocamidopropyl Betaine [6] | 2 |
|   | Dimethicone (&) C12-13 Pareth-4 (&) C12-13 Pareth-23 (&) Salicylic Acid [7] | 2.5 |
| D | Cetyl Alcohol [8] | 1.2 |
|   | Cocamide MEA [9] | 1.5 |
|   | Glycol Distearate [10] | 2 |

TABLE 7-continued

Composition of the pearly isotropic shampoo formulation

| Phases | Ingredients | Concentration (% wt) |
|---|---|---|
| E | Methylchloroisothiazolinone & Methylisothiazolinone [11] | 0.1 |
|  | D-Panthenol 75% [12] | 0.1 |
|  | Water deionized | 0.3 |
| F | Sodium Chloride 25% aqueous sol. | 0.6 |

[1] EDETA B Powder, Origin: BASF
[2] Jaguar C14 S, Origin: Rhodia
[3] Ucare Polymer JR-400, Origin: Noveon
[4] Sulfetal LA B-E, Origin: Zschimmer & Schwarz
[5] Zetesol LA, Origin: Zschimmer & Schwarz
[6] Tego Betain F 50, Origin: Evonik
[7] Xiameter MEM-1691, Origin: Dow Corning
[8] Lanette 16, Origin: BASF
[9] Comperlan 100, Origin: Cognis
[10] Cutina AGS, Origin: Cognis
[11] Kathon CG, Origin: Rohm & Haas
[12] D-Panthenol, Origin: Roche The shampoo was prepared by dispersed in water and Tetrasodium EDTA, Guar Hydroxypropyltrimonium Chloride and Polyquatemium-10. NaOH 10% solution (Phase B) was added once Phase A was homogeneous. Then, the premixed Phase C was added. and mixture was heated to 75° C. Phase D ingredients were added and mixed till homogeneous. The mixture was cooled down. At 45° C., Phase E ingredients were added while mixing. Final viscosity was adjusted with 25% NaCl solution and pH of 5.5-6 was adjusted with 10% NaOH solution.

The perfumed pearly shampoo was prepared by adding 0.4 to 0.8% by weight, relative to the total weight of the shampoo, of the invention's composition of example 3 into the unperfumed shampoo formulation of Table 7 under gentle shaking.

Example 11

Preparation of a Structured Shower Gel Comprising the Invention's Composition

TABLE 8

Composition of the milky shower gel formulation

| Ingredients | Amount (% wt) |
|---|---|
| WATER deionised | 49.350 |
| Tetrasodium EDTA [1] | 0.050 |
| Acrylates Copolymer [2] | 6.000 |
| Sodium C12-C15 Pareth Sulfate [3] | 35.000 |
| Sodium Hydroxide 20% aqueous solution | 1.000 |
| Cocamidopropyl Betaine [4] | 8.000 |
| Methylchloroisothiazolinone and Methylisothiazolinone [5] | 0.100 |
| Citric Acid (40%) | 0.500 |

[1] EDETA B POWDER; trademark and origin: BASF
[2] CARBOPOL AQUA SF-1 POLYMER; trademark and origin: NOVEON
[3] ZETESOL AO 328 U; trademark and origin: ZSCHIMMER & SCHWARZ
[4] TEGO-BETAIN F 50; trademark and origin: GOLDSCHMIDT
[5] KATHON CG; trademark and origin: ROHM & HASS The transparent shower gel was prepared by adding 0.5 to 1.5% by weight, relative to the total weight of the shower gel, of the invention's composition of example 3 into the unperfumed shower gel formulation of Table 8 under gentle shaking.

What is claimed is:

1. A compound of formula

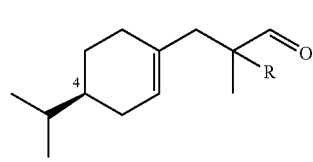

(I)

in the form of any one of its stereoisomers or as a mixture thereof, and wherein carbon 4 of the cyclohexenyl group has an absolute S configuration and R represents a hydrogen atom or a methyl group.

2. The compound according to claim 1, characterized in that, the compound of formula (I) is of formula

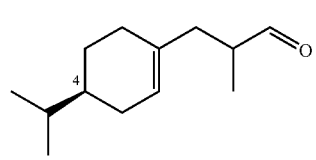

(II)

in the form of any one of its stereoisomers or as a mixture thereof, and wherein carbon 4 of the cyclohexenyl group has an absolute S configuration.

3. A method to confer, enhance, improve or modify the odor properties of a perfuming composition or of a perfumed article, which method comprises adding to said composition or article an effective amount of at least a compound of formula (I) as defined in claim 1.

4. A perfuming ingredient comprising a compound of formula (I) as defined in claim 1.

5. A perfuming composition comprising
   i) at least one compound of formula (I), as defined in claim 1;
   ii) at least one ingredient selected from the group consisting of a perfumery carrier and a perfumery base; and
   iii) optionally at least one perfumery adjuvant.

6. A perfumed consumer product comprising a composition as defined in claim 5.

7. The perfumed consumer product according to claim 6, wherein the product is a perfume, a fabric care product, a body-care product, a cosmetic preparation, a skin-care product, an air care product or a home care product.

8. The perfumed consumer product according to claim 7, wherein the perfumery consumer product is a fine perfume, a splash or eau de perfume, a cologne, an shave or aftershave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care products, a hygiene product, an air freshener, a "ready to use" powdered air freshener, a mold remover, a furnisher care, a wipe, a dish detergent or hard-surface detergent, a leather care product or a car care product.

9. A perfumed consumer product comprising at least one compound of formula (I), as defined in claim 1.

10. The perfumed consumer product according to claim 9, wherein the product is a perfume, a fabric care product, a body-care product, a cosmetic preparation, a skin-care product, an air care product or a home care product.

11. The perfumed consumer product according to claim 10, wherein the perfumery consumer product is a fine perfume, a splash or eau de perfume, a cologne, an shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care products, a hygiene product, an air freshener, a "ready to use" powdered air freshener, a mold remover, a furnisher care, a wipe, a dish detergent or hard-surface detergent, a leather care product or a car care product.

* * * * *